United States Patent [19]

Lalk et al.

[11] 4,356,309
[45] Oct. 26, 1982

[54] N-ALKYLATED 2-(2-PYRIDYL)IMIDAZOLES USEFUL AS METALLURGICAL EXTRACTANTS

[75] Inventors: James W. Lalk, Shepherd; Frances P. Hamburg, Midland, both of Mich.

[73] Assignee: The Dow Chemical Company, Midland, Mich.

[21] Appl. No.: 282,628

[22] Filed: Jul. 13, 1981

[51] Int. Cl.³ .......................................... C07D 401/04
[52] U.S. Cl. .................................................. 546/278
[58] Field of Search ........................................ 546/278

[56] References Cited

U.S. PATENT DOCUMENTS 4,202,944  5/1980  Hancock ............................... 521/32
4,254,087  3/1981  Grinstead .............................. 423/24

OTHER PUBLICATIONS

Chriswell et al, Inorganic Chemistry, vol. 3, No. 1, (1964), pp. 110–114.
Sawa et al, Chemical Abstracts, vol. 67, (1967) 54128z.

*Primary Examiner*—Richard Raymond
*Attorney, Agent, or Firm*—John M. Sanders

[57] ABSTRACT

Compounds of the formula

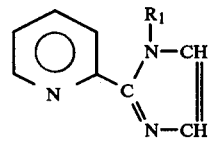

wherein $R_1$ represents
 $C_1$ to $C_{20}$ alkyl-substituted benzyl, or
 $C_2$ to $C_{20}$ alkyl which can optionally bear one or two
  —$OR_2$ radicals, wherein each $R_2$ independently
  represents hydrogen or the radical

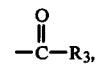

wherein $R_3$ represents $C_1$ to $C_{20}$ alkyl are disclosed. These compounds are useful for the selective extraction of cobalt, nickel or copper ions from aqueous acidic ore leach liquors.

6 Claims, No Drawings

N-ALKYLATED 2-(2-PYRIDYL)IMIDAZOLES USEFUL AS METALLURGICAL EXTRACTANTS

SUMMARY OF THE INVENTION

The present invention relates to an N-alkylated 2-(2-pyridyl)imidazole compound of the formula

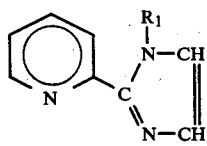

wherein $R_1$ represents $C_1$ to $C_{20}$ alkyl-substituted benzyl, or $C_2$ to $C_{20}$ alkyl which can optionally bear one or two —$OR_2$ radicals, wherein each $R_2$ independently represents hydrogen or the radical

wherein $R_3$ represents $C_1$ to $C_{20}$ alkyl.

These compounds are useful as chelating agents for selectively extracting cobalt, copper or nickel from aqueous media when said compounds are dissolved in an appropriate organic solvent.

DESCRIPTION OF THE PREFERRED EMBODIMENTS

For convenience the compounds of the present invention are identified as N-alkylated 2-(2-pyridyl)imidazoles.

The N-alkylated 2-(2-pyridyl)imidazoles of the present invention can be prepared by methods analogous to those known in the art to prepare related materials. For example, the N-alkylated 2-(2-pyridyl)imidazoles, where $R_1$ is a substituted benzyl or unsubstituted alkyl, are prepared by reacting 2-(2-pyridyl)imidazole with an appropriate benzyl halide or alkyl halide in the presence of a solvent and base. When $R_1$ of Formula I is a hydroxyalkyl, i.e., $R_2$ is H, the 2-(2-pyridyl)imidazole is reacted with an appropriate epoxide, preferably neat. When $R_1$ of Formula I is an ester of a hydroxyalkyl, i.e. $R_2$ is

an appropriate N-hydroxyalkyl-2-(2-pyridyl)imidazole, prepared as above, is reacted with an appropriate acid chloride having $R_3$ as the alkyl portion in the presence of a solvent.

In carrying out the reaction where $R_1$ is benzyl or alkyl, the 2-(2-pyridyl)imidazole starting material is dissolved in a solvent such as, for example, acetonitrile, in the presence of a base such as, KOH. To this mixture is added the requisite alkyl halide or benzyl halide. The reactants are maintained under agitation during the reaction period. The reaction is carried out at temperatures between about 25° C. and about 200° C. and depending upon the specific reactants and solvent employed, the reaction is usually complete in from about ½ to about 25 hours. Upon completion of the reaction, the reaction mixture is cooled and the desired product recovered by filtration or other conventional separatory techniques. The product can then be purified by conventional techniques such as, for example, extraction with a solvent, such as hexane.

When the desired product is a compound of Formula I where $R_1$ is a hydroxyalkyl, i.e., $R_2$ is H, the reaction is run neat, i.e., without a solvent, and is initiated by the addition of a small quantity of water. Thus, in carrying out the reaction the 2-(2-pyridyl)imidazole and an appropriate epoxide are mixed and then a few drops of water are added to initiate the reaction. The reactants are maintained under agitation during the reaction period. The reaction is carried out at temperatures between about 25° C. and about 200° C. under an inert atmosphere such as nitrogen, and the reaction is usually complete in from about ¼ to about 25 hours. Upon completion of the reaction, the reaction mixture is cooled and the desired product is recovered by extraction with a solvent such as, hexane.

When the desired product is a compound of Formula I where $R_1$ is an ester of a hydroxyalkyl, i.e., $R_2$ is

an appropriate acid chloride is added to a solution of a N-hydroxyalkyl-2-(2-pyridyl)imidazole, the preparation of which is described hereinbefore, in a solvent such as pyridine. The reactants are maintained under agitation during the reaction period. The reaction is carried out at temperatures between about 25° C. and reflux. Depending upon the specific reactants and solvent employed, the reaction is usually complete in from about ½ to about 25 hours. Upon completion of the reaction, the reaction mixture is cooled and the desired product recovered using conventionally known techniques such as distillation or solvent extraction.

Representative compounds of Formula I include compounds wherein $R_1$ is:

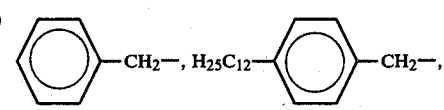

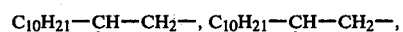

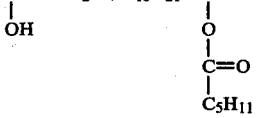

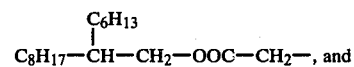

(from epoxidized soy oil).

The N-alkylated 2-(2-pyridyl)imidazoles are useful as chelating amines in a metallurgical extractant system described in U.S. Pat. No. 4,254,087 which is incorporated herein by reference. Said metallurgical extractant system is used to selectively extract cobalt, copper or nickel from aqueous acidic ore leach liquors containing the same and having a pH of below about 3.0. The extractant system has superior selectivity and/or activity in the recovery of desired metal values, e.g., cobalt, nickel and/or copper alone or from mixtures with each other and/or non-desired metal values, such as aluminum, calcium, iron, magnesium and manganese and comprises (a) a high molecular weight alkyl aromatic sulfonic acid, (b) a chelating amine and (c) a solvent which is essentially immiscible with water. High selectivity ratios of the desired metals over the non-desired metals, e.g., a Cu:Fe ratio of about 2000 or more, can be obtained by use of the extractant system. The extractant system also possesses highly advantageous properties in that cobalt and nickel can be selectively extracted from acid solutions below about pH 2 in preference to iron.

The process for recovering a desirable metal value selected from the group consisting of cobalt, copper and nickel from an acidic, aqueous ore leach liquor containing said desired metal value and non-desired metal value comprises (1) contacting said leach liquor at a pH of below about 3.5 with a solvent-extractant system comprising (a) a high molecular weight alkylaromatic sulfonic acid, (b) a chelating amine, and (c) a water-immiscible solvent for (a), (b) and metal complexes of (a) and (b) to provide a solution of the desired metal value in the extractant but not the non-desired metal value in appreciable amount, (2) separating the thus-formed solution from the aqueous raffinate depleted in the desired metal value, and (3) recovering the desired metal value from the separated solution.

In the foregoing Formula I, the alkyl moieties can be straight- or branched-chain and the benzyl and pyridyl moieties can also be further substituted with moieties which are not detrimental to the activity of the compound as part of the extractant system described herein. Preferred compounds include those wherein $R_1$ is a branched chain alkyl group containing from about 12 to about 20 carbon atoms.

The following examples illustrate the present invention, which is limited only by the limits of the appended claims.

EXAMPLE 1—Preparation of 1-dodecyl-2-(2-pyridyl)imidazole

A mixture of 14.5 g (0.1 mole) 2-(2-pyridyl)imidazole, 6 g (0.11 mole) ground KOH, 30 g (0.1 mole) iododecane in about 150 ml of acetonitrile was stirred and refluxed for about 2 hours. The iododecane gradually went into solution as the reaction proceeded. After the 2 hours the reaction mixture was cooled and filtered. The resulting residue was extracted with hexane to give 32.5 g of crude product.

EXAMPLE 2—Preparation of 1-(2-hydroxydodecyl)-2-(2-pyridyl)imidazole

A mixture of 14.5 g (0.1 mole) 2-(2-pyridyl)imidazole, 18.4 g (0.1 mole) 1,2-epoxydodecane and 3 drops of water was heated with stirring at about 160° C. under nitrogen for about one hour. The resulting product was then extracted with hot hexane and collected as yellow crystals which had a melting point of 62°–65° C.

EXAMPLE 3

In testing the N-alkylated 2-(2-pyridyl)imidazoles of the present invention in extractant systems, known techniques such as generally described hereinbelow are employed.

Reagent grade metal sulfate salts and sulfuric acid were used to prepare aqueous stock solutions (synthetic leach) containing about 1 gram/liter each of two or more various metal ions, such as cupric copper, ferric, nickel, cobalt and/or aluminum ions. Equal aliquots of the metal ion stock solutions desired are then mixed and either dilute sulfuric acid, water, or dilute sodium carbonate solutions are added to give an adjusted final aqueous volume of about 60 milliliters (ml) and an initial pH in the range of 2 to 5. This solution is then mixed with 20 ml of an extractant system comprising a solution of the chelating amine and the alkylaromatic sulfonic acid in an inert solvent and the resulting mixture is vigorously mixed by using mechanical agitation means until the equilibrium pH of the mixture is attained. The two phases are then carefully separated, with the organic phase being stripped with sulfuric acid (1 to 3 N). The metal ion concentration of the raffinate is determined by atomic absorption spectrometry. The metal ion concentration in the organic phase is determined by the difference in concentration between the feed and aqueous raffinate concentrations. The distribution coefficient ($D_a^o$) of the organic (o) to aqueous (a) phases for each metal is then calculated.

In operations utilizing the foregoing general procedures, 20 ml of a 0.20 M solution of N-(2-hydroxydodecyl)-2-(2-pyridyl)imidazole and 0.20 M dinonylnaphthalene sulfonic acid (DNNSA) in an aliphatic diluent NAPOLEUM 470 (Kerr McGee Corp.) were mixed with 60 ml of an acidic aqueous solution containing 1.0 gram per liter each of iron and copper ions (for Run No. 1) and nickel, cobalt and aluminum ions (for Run No. 2), all as the sulfates, and mixed for about 2–3 minutes until an equilibrium pH of about 1.6 was attained. Separation and analysis of the aqueous and organic phases carried out as described above gave the following results including the equilibrium pH and distribution coefficients, which are set forth below in Table I:

TABLE I

| No. | Chelating Amine | Final pH | $D_a^o$ Metal Ion | | | | |
| --- | --- | --- | --- | --- | --- | --- | --- |
| | | | Cu | Fe | Ni | Co | Al |
| 1 | N-(2-hydroxy-dodecyl)-2-(2-pyridyl)imidazole | 1.6 | 230 | 0.004 | — | — | — |
| 2 | N-(2-hydroxy-dodecyl)-2-(2-pyridyl)imidazole | 2.1 | — | — | 0.5 | 1.23 | 0.024 |

Where a specific equilibrium pH was desired, dilute (ca 1N) sulfuric acid or sodium hydroxide was added until the desired pH was obtained and remained constant for 5 minutes.

EXAMPLE 4

Employing substantially the same procedure of Example 3 the following N-alkylated 2-(2-pyridyl)imidazoles were employed as extractants from an aqueous solution containing 1 gram/liter each of 3 ions: nickel, iron (III), cobalt (II) or aluminum, present as the sulfate salts. The results ae indicated in Table II according to the particular N-alkylated 2-(2-pyridyl)imidazole

TABLE II

| Substituent R₁ | Diluent | Final pH | Distribution Ratio | | | |
|---|---|---|---|---|---|---|
| | | | Ni | Co | Al | Fe(III) |
| 2-hydroxydodecyl | *N470 | 2.1 | 0.50 | 1.23 | 0.024 | —*** |
| | **Cyclo 52 | 2.2 | 0.32 | 1.1 | — | 0.003 |
| Dodecyl | N470 | 1.75 | 0.49 | 0.74 | 0.005 | — |
| 4-Dodecylbenzyl | N470 | 1.70 | 0.61 | 1.06 | 0.005 | — |
| $C_5H_{11}COO$<br>\|<br>$C_{10}H_{21}$—CH—CH₂— | N470 | 1.8 | 0.18 | 0.53 | 0.009 | — |
| $C_6H_{13}$<br>\|<br>$C_8H_{17}$—CH—CH₂—OOC—CH₂— | N470 | 1.7 | 0.25 | 0.22 | 0.014 | — |
| OH<br>\|<br>$C_{18}H_{14}$—CH—CH—$C_7H_{14}COOCH_3$<br>\| | Cyclo 52 | 1.7 | 11.2 | 0.15 | 0.075 | — |

(from epoxidized soy oil)

*N470 denotes Napoleum 470, an aliphatic diluent made by Kerr-McGee Oil Co.
**Cyclo 52 denotes Cyclosol 52, an aromatic diluent made by Shell Oil Co.
—*** denotes absence of metal ion in the aqueous solution employed in the particular test.

We claim:

1. A compound of the formula

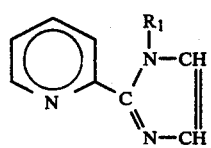

(I)

wherein R₁ represents
C₁ to C₂₀ alkyl-substituted benzyl, or
C₁₂ to C₂₀ alkyl which can optionally bear one or two —OR₂ radicals, wherein each R₂ independently represents hydrogen or the radical

wherein R₃ represents C₁ to C₂₀ alkyl.

2. The compound of claim 1 wherein R₁ is a branched chain alkyl group.

3. The compound of claim 2 wherein R₁ has from about 12 to about 20 carbon atoms.

4. The compound of claim 1 which is 1-dodecyl-2-(2-pyridyl)imidazole and which corresponds to the formula

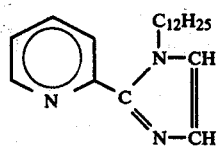

5. The compound of claim 1 which is 1-(2-hydroxydodecyl)-2-(2-pyridyl)imidazole and which corresponds to the formula

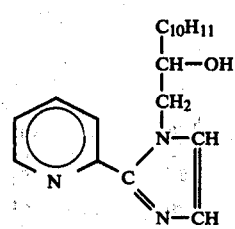

6. The compound of claim 1 which is 1-[2-hexanoyloxy)dodecyl]-2-(2-pyridyl)imidazole and corresponds to the formula

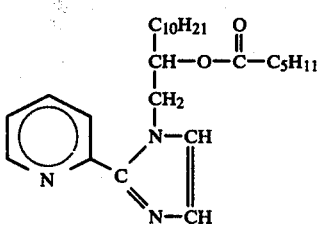

* * * * *